United States Patent [19]

Araki et al.

[11] Patent Number: 4,618,607
[45] Date of Patent: Oct. 21, 1986

[54] 1,4-DIHYDROPYRIDINE-3,5-DICARBOXYLIC ACID ESTER DERIVATIVES AND PHARMACEUTICAL COMPOSITIONS

[75] Inventors: Kazuhiko Araki; Hideki Ao, both of Nakatsu; Jun Inui, Tokyo; Kenichi Aihara, Fukuoka, all of Japan

[73] Assignee: Yoshitomi Pharmaceutical Industries, Ltd., Osaka, Japan

[21] Appl. No.: 448,576

[22] Filed: Dec. 10, 1982

[30] Foreign Application Priority Data

Mar. 17, 1982 [WO] PCT Int'l Appl. ... PCT/JP82/00075

[51] Int. Cl.$^4$ .................. A61K 31/445; A61K 31/55; C07D 401/12; C07D 401/14
[52] U.S. Cl. ..................................... 514/212; 514/222; 514/228; 514/230; 514/232; 514/233; 514/236; 514/252; 514/256; 514/278; 514/318; 514/333; 544/58.6; 544/82; 544/122; 544/131; 544/295; 544/333; 544/365; 546/19; 546/187; 546/193; 546/194; 546/256; 546/257; 546/258; 546/263; 546/275; 546/278; 546/280; 260/243.3; 260/244.4
[58] Field of Search ............... 544/58.6, 82, 122, 131, 544/295, 333, 365; 546/19, 256, 257, 258, 263, 275, 278, 280, 283, 284, 187, 193, 194, 281; 260/243.3, 244.4; 424/246, 248.5, 248.51, 248.52, 248.54, 248.55, 250, 251, 266; 514/212, 222, 228, 230, 232, 233, 236, 252, 256, 278, 318, 333

[56] References Cited

U.S. PATENT DOCUMENTS 4,038,399 7/1976 Bossert et al. .............. 546/281
4,450,165 5/1984 Araki et al. .............. 546/281

FOREIGN PATENT DOCUMENTS 1383625 2/1975 United Kingdom .

OTHER PUBLICATIONS

Araki et al, European Patent Application 60,897 (9-2-9-82).
Wehinger et al, *Chemical Abstracts*, vol. 95 (1981), No. 42922ec.
Central Patents Index Abstracts, No. 21613, D/13 (1981).
Yoshitomi, *Chemical Abstracts*, vol. 96 (1982), No. 199,719b; Substance Index, vol. 96, pp. 5774cs, 1279cs.

*Primary Examiner*—Robert W. Ramsuer
*Attorney, Agent, or Firm*—Sughrue, Mion, Zinn, Macpeak & Seas

[57] ABSTRACT

1,4-Dihydropyridine-3,5-dicarboxylic acid ester derivatives of the general formula:

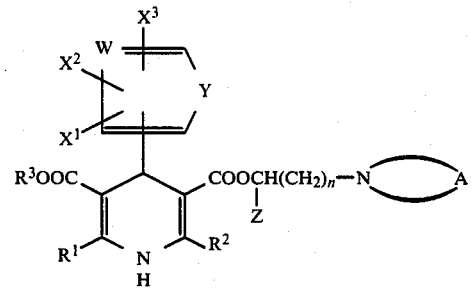

or acid addition salts thereof, wherein W is —CH= or —N=; Y is —CH=CH—, —O—, —S—, —CH=N(O)p— (p is zero or 1) or —N(R)— (R is hydrogen or lower alkyl); $X^1$, $X^2$ and $X^3$ are the same or different, and are each hydrogen, halogen, nitro, trifluoromethyl, cyano or lower alkylthio; Z is aryl or 5- or 6-membered aromatic heterocyclic ring (which may have a substituent or two or three substituents which may be the same or different, and the substituent may be halogen, lower alkyl, lower alkoxy, lower alkanoylamino, cyano, nitro, lower alkylthio, trifluoromethyl, sulfamoyl, di-lower alkylsulfamoyl, amino or di-lower alkylamino);

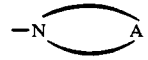

is 5- to 7-membered heterocyclic ring which may have nitrogen atom, oxygen atom, sulfur atom or unsaturated bond on the ring, and may be substituted by lower alkyl, lower alkoxycarbonyl, lower alkanoylamino, ethylenedioxy or —(CH$_2$)$_m$—OR$^4$ (R$^4$ is hydrogen, lower alkyl or lower alkanoyl and m is 0, 1 or 2); $R^1$ and $R^2$ are the same or different, and are each lower alkyl; $R^3$ is lower alkyl, aralkyl, heteroaralkyl; and n is an integer 1 to 5. Such compounds are useful as antihypertensive agents and as therapeutic agents for cardiac and cerebral circulation disorders.

7 Claims, No Drawings

1,4-DIHYDROPYRIDINE-3,5-DICARBOXYLIC ACID ESTER DERIVATIVES AND PHARMACEUTICAL COMPOSITIONS

This invention relates to novel 1,4-dihydropyridine-3,5-dicarboxylic acid ester derivatives of the general formula:

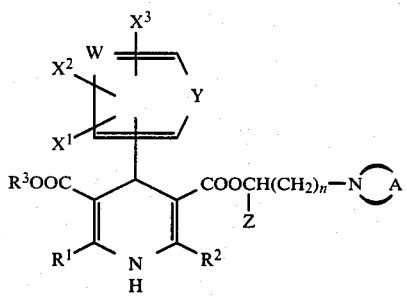

and the salts thereof which are useful as medicines and to the methods for the production thereof.

In the formula, the symbols are each as follows: W represents —CH= or —N=; Y represents —CH=CH—, —O—, —S—, —CH=N(O)$_p$— (wherein p represents zero or 1) or —N(R)— (wherein R represents hydrogen or lower alkyl, e.g. methyl, ethyl, propyl, isopropyl or butyl; $X^1$, $X^2$ and $X^3$ are the same or different and represent each hydrogen, halogen (fluorine, bromine, chlorine or iodine), nitro, trifluoromethyl, cyano or lower alkylthio (e.g. methylthio, ethylthio, propylthio, isopropylthio or butylthio); Z represents aryl (e.g. phenyl) or 5- or 6-membered aromatic heterocyclic ring (e.g. thienyl, furyl, pyridyl, thiazolyl, oxazolyl, pyrimidinyl, isoxazolyl, pyrrolyl or imidazolyl) which may have a substituent or two or three substituents (which may be the same or different) and, as the substituents, there may be mentioned halogen (fluorine, bromine, chlorine or iodine), lower alkyl (e.g. methyl, ethyl, propyl, isopropyl or butyl), lower alkoxy (e.g. methoxy, ethoxy, propoxy, isopropoxy or butoxy), lower alkanoylamino (e.g. acetylamino, propionylamino or butyrylamino), cyano, nitro, lower alkylthio (e.g. methylthio, ethylthio, propylthio, isopropylthio or butylthio), trifluoromethyl, sulfamoyl, di-lower alkylsulfamoyl (e.g. dimethylsulfamoyl, diethylsulfamoyl, dipropylsulfamoyl, diisopropylsulfamoyl or dibutylsulfamoyl), amino and di-lower alkylamino (e.g. dimethylamino, diethylamino, dipropylamino, diisopropylamino, or dibutylamino);

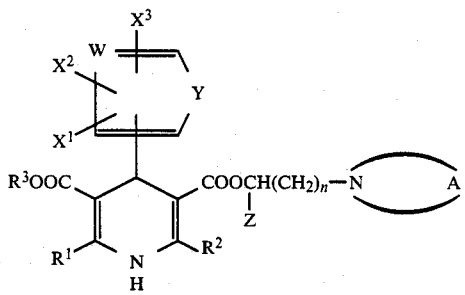

represents 5- to 7-membered heterocyclic ring which may comprise nitrogen atom, oxygen atom, sulfur atom or unsaturated bond(s) on the ring (e.g. 1-pyrrolidinyl, piperidino, hexahydroazepin-1-yl, morpholino, thiomorpholino, 1-piperazinyl or 1,2,3,6-tetrahydro-1-pyridyl) and may be substituted by lower alkyl (e.g. methyl, ethyl, propyl, isopropyl or butyl), lower alkoxycarbonyl (e.g. methoxycarbonyl, ethoxycarbonyl, propoxycarbonyl, isopropoxycarbonyl or butoxycarbonyl), lower alkanoylamino (e.g. acetylamino, propionylamino, butyrylamino), ethylenedioxy, —(CH$_2$)$_m$—OR$^4$— [wherein R$^4$ represents hydrogen, lower alkyl (e.g. methyl, ethyl, propyl, isopropyl or butyl), lower alkanoyl (e.g. acetyl, propionyl or butyryl) and m represents 0, 1 or 2]; R$^1$ and R$^2$ are the same or different and represent each lower alkyl (e.g. methyl, ethyl, propyl, isopropyl or butyl); R$^3$ represents lower alkyl (methyl, ethyl, propyl, isopropyl, or butyl), aralkyl (benzyl, phenetyl or phenylpropyl which may be substituted by one or two of, for example, chlorine, fluorine, methyl or methoxy), heteroaralkyl (e.g. furylmethyl, thienylmethyl or pyridylmethyl); and n represents an integer 1 to 5.

The compounds (I) of this invention exhibit strong vasodilating and antihypertensive activities and, therefore, are useful as antihypertensive agents and therapeutic agents for cardiac and cerebral circulation disorders.

This invention has been accomplished on the basis of the new findings that the introduction of the aromatic ring or aromatic heterocyclic ring at α-position of the cyclic aminoalkylester moiety in the side chain causes increased and remarkably prolonged effectiveness.

According to this invention, the compounds of the general formula (I) can be produced by, for example, the following methods:

Method 1

A new method which comprises reacting a compound of the general formula:

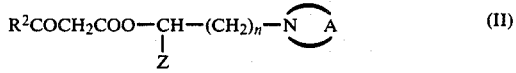

wherein the symbols are each the same as defined above, with a compound of the general formula:

wherein the symbols are each the same as defined above, and a compound of the general formula:

wherein the symbols are each the same as defined above.

This reaction is carried out by mixing the compounds of the general formulas (II), (III) and (IV) and heating the mixture in the presence of an appropriate solvent (e.g. methanol, ethanol, propanol, isopropanol, dioxane, benzene, toluene, acetonitrile, dimethylformamide or dimethyl sulfoxide).

The compounds (IV) can be obtained by, for example, preliminarily reacting a compound of the formula: $R^1$—$COCH_2COOR^3$ with ammonia. The resultant compound of this reaction may be once isolated, followed by the reaction with the compounds (II) and (III) or be subjected directly to the following reaction as it is without being isolated to yield the object compound (I).

Method 2

A method which comprises reacting a compound of the general formula:

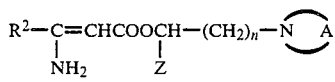

(V)

wherein the symbols are each the same as defined above, with a compound of the general formula (III) and a compound of the general formula:

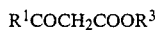 (VI)

wherein the symbols are each the same as defined above.

This reaction is carried out by mixing the compounds of the general formulas (V), (III) and (VI) and heating the mixture in the presence of an appropriate solvent (such as defined above). The compounds (V) can be obtained by, for example, preliminarily reacting a compound (II) with ammonia. The resulting compound of this reaction may be once isolated, followed by the reaction with the compounds (III) and (VI) or be subjected directly to the following reaction as it is without being isolated to yield the object compound (I).

Method 3

A method which comprises reacting a compound of the general formula (IV) with a compound of the general formula:

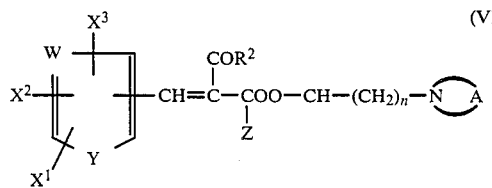 (VII)

wherein the symbols are each the same as defined above, which can be obtained by preliminarily reacting a compound of the general formula (II) with a compound of the general formula (III).

This reaction is carried out by heating the mixture in the presence of an appropriate solvent (such as defined above). The compound of the general formula (VII) may be once isolated, followed by the reaction with the compound (IV) or be subjected directly to the following reaction as it is without being isolated.

Method 4

A method which comprises reacting a compound of the general formula (V) with a compound of the general formula:

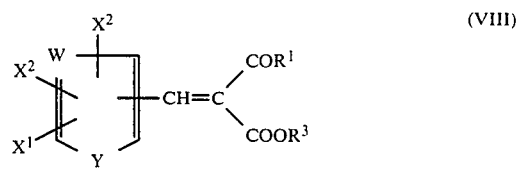 (VIII)

wherein the symbols are each the same as defined above, which can be obtained by preliminarily reacting a compound of the general formula (III) with a compound of the general formula (VI).

This reaction is carried out by heating the mixture in the presence of an appropriate solvent (such as defined above). The compound of the general formula (VIII) may be once isolated, followed by the reaction with the compound (V) or be subjected directly to the following reaction as it is without being isolated.

Method 5

A method which comprises reacting a compound of the general formula:

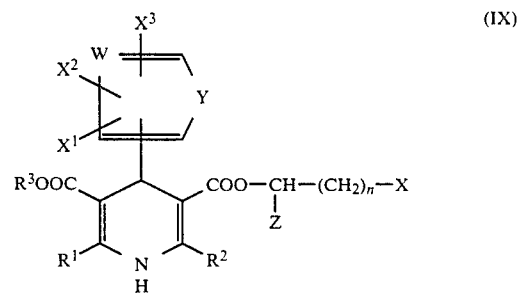 (IX)

wherein X represents an acid residue of an active ester (e.g. halogen such as chlorine, bromine, iodine or alkylsulfonyloxy or arylsulfonyloxy such as methylsulfonyloxy, ethylsulfonyloxy, benzenesulfonyloxy, or p-toluenesulfonyloxy) and the other symbols are the same as defined above, with a compound of the general formula:

 (X)

wherein

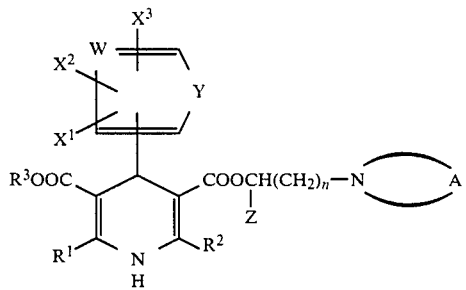

is the same as defined above.

This reaction is carried out in an appropriate solvent (such as defined above) in the presence of an acid acceptor agent (an inorganic alkali such as alkali carbonate, alkali bicarbonate or alkalialcolate, or an organic base such as triethylamine, dimethylaniline, diethylaniline or pyridine). The reaction is usually conducted at about room temperature to about the boiling point of the solvent for several to scores of hours. The compounds of the general formula (IX) can be readily obtained by, for example, the above-mentioned Methods 1 to 4 using a compound of the general formula:

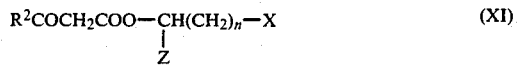
(XI)

wherein the symbols are each the same as defined above) as a starting compound.

Method 6

A method which comprises reacting a compound of the general formula:

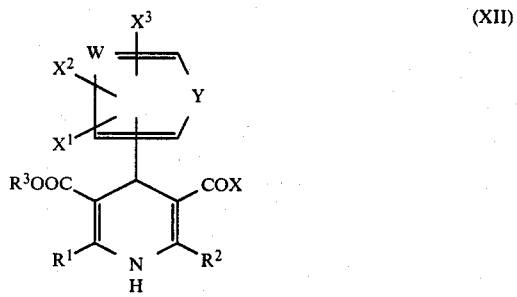
(XII)

wherein the symbols are each the same as defined above, with a compound of the general formula:

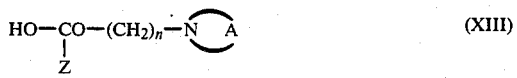
(XIII)

wherein the symbols are each the same as defined above.

This reaction is conducted in the same manner as mentioned in above Method 5.

The compounds of the general formula (I) thus obtained can be isolated and purified by the conventional chemical procedures.

. The compounds of the present invention have asymmetric carbon atoms and therefore are present as optically active isomers or as mixtures thereof. All of these are within the scope of this invention. The racemic compounds may, if desired, for example, be resolved by formation of diastereoisomers with an optically active acid compound (e.g. tartaric acid, diacetyltartaric acid, tartranilic acid, dibenzoyl tartaric acid or ditoluoyltartaric acid), followed by crystallization, distillation, chromatography and so forth. The salts thus resolved give optically active bases. By the use of an optically active starting compound, the final product of desired configuration can be produced stereo-selectively.

The compounds of this invention can be converted into an inorganic or organic salt thereof such as hydrochloride, hydrobromide, phosphate, sulfate, oxalate, maleate, fumarate, tartrate, acetate.

The compounds of this invention have, for example, excellent increasing activity in vetebral blood flow and coronary blood flow in dogs, increasing activity in cerebral blood flow in rabbits and antihypertensive activity against spontaneously hypertensive rats and further are characteristic of remarkably prolonged duration of such activities.

When the compounds of this invention are used as medicines, they can be administered orally or parenterally as they are or in any form of such as tablets, capsules, granules, powders or injectable solutions prepared by mixing with pharmacologically acceptable and suitable excipients, carriers, diluents and the like. The daily dose for human adults ranges from about 1 mg to about 50 mg for oral administration in single or multiple dose.

The dose, however, may vary depending upon the age, body weight and/or severity of the condition to be treated as well as the response to the medication.

The following examples given to describe the present invention in more detail, but should not be considered as limiting this invention.

In the following examples, when two kinds of diastereoisomers are obtained, the diastereoisomer which shows a spot appearing at the upper part by thin layer chromatography is referred to as "α-diastereoisomer" and the diastereoisomer which shows a spot appearing at the lower part is referred to as "β-diastereoisomer".

EXAMPLE 1

In 300 ml of isopropanol are dissolved 28.9 g of 1-phenyl-2-piperidinoethyl acetoacetate, 15.1 g of m-nitrobenzaldehyde and 11.5 g of methyl β-aminocrotonate, and the mixture is refluxed under heating for 17 hours. The reaction mixture is concentrated under reduced pressure and the residue is purified by column chromatography on silica gel (eluent:chloroform:methanol=10:1 (by volume)). The eluate containing the object compound is concentrated and recrystallized from isopropanol to give 2,6-dimethyl-4-(m-nitrophenyl)-1,4-dihydropyridine-3,5-dicarboxylic acid-3-methylester-5-(1-phenyl-2-piperidinoethyl)ester as crystals melting at 183°-185° C. (decomposition). This is α-diastereoisomer. The hydrochloride thereof melts at 238°-240° C. (decomposition). The β-diastereoisomer which can be obtained in similar manner melts at 127°-130° C. (from isopropanol), and the hydrochloride thereof melts at 222°-223° C. (decomposition) (from ethanol).

The compound of Example 1 which is represented by the formula:

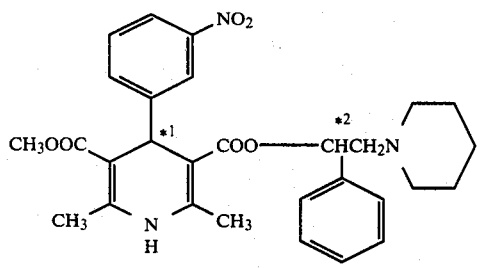

wherein the asterisks indicate asymmetric carbon atoms, has two asymmetric carbon atoms, and therefore, four kinds of stereoisomers. These stereoisomers can be produced by subjecting to usual optical resolution the α or β-diastereoisomer thus obtained, or by using corresponding starting materials in which one or both of the asymmetric carbon atoms marked "*1" and "*2" in the formula are optically active (when the diastereoisomer is obtained, this is separated).

These isomers are summarized below:

(A) (4S)-2,6-dimethyl-4-(m-nitrophenyl)-1,4-dihydropyridine-3,5-dicarboxylic acid-3-methylester-5-[(1R)-1-phenyl-2-piperidinoethyl]ester, m.p. 169°–170° C. (decomposition), $[\alpha]_D^{25}+201.9°$ (c=1.0, methanol)

(B) (4R)-2,6-dimethyl-4-(m-nitrophenyl)-1,4-dihydropyridine-3,5-dicarboxylic acid-3-methylester-5-[(1S)-1-phenyl-2-piperidinoethyl]ester, m.p. 169°–171° C. (decomposition), $[\alpha]_D^{25}-201.2°$ (c=1.0, methanol)

(C) (4S)-2,6-dimethyl-4-(m-nitrophenyl)-1,4-dihydropyridine-3,5-dicarboxylic acid-3-methylester-5-[(1S)-phenyl-2-piperidinoethyl]ester, m.p. 143° C., $[\alpha]_D^{25}-5.09°$ (c=2.5, chloroform)

(D) (4R)-2,6-dimethyl-4-(m-nitrophenyl)-1,4-dihydropyridine-3,5-dicarboxylic acid-3-methylester-5-[(1R)-1-phenyl-2-piperidinoethyl]ester, m.p. 143° C., $[\alpha]_D^{25}+5.42°$ (c=2.5, chloroform)

EXAMPLE 2

To 90 ml of chloroform is added 5.4 g of 2,6-dimethyl-4-(m-nitrophenyl)-1,4-dihydropyridine-3,5-dicarboxylic acid-monomethylester, whereupon 3.7 g of phosphorous pentachloride is added at once under ice-cooling at 0° C. to 5° C. The mixture is stirred at 0° C. to 5° C. for an hour. The resulting acid chloride is, without being isolated, cooled to −40 C. on the dry ice-methanol bath, followed by dropwise addition of a solution of 13.6 g of 1-phenyl-2-(4-ethoxycarbonyl-1-piperazinyl)ethanol in 30 ml of chloroform over the period of 30 minutes. The whole is allowed to stand for cooling. After it reached 0° C., it is stirred under ice-cooling for two hours. Then, the chloroform layer is washed with a 5% aqueous solution of sodium carbonate, a 5% aqueous solution of hydrochloric acid, and a 5% aqueous solution of sodium carbonate. The chloroform layer is dried over magnesium sulfate and the chloroform is distilled off under reduced pressure. The residue is dissolved in acetone whereupon an ethanol solution of hydrogen chloride is added. The whole is allowed to stand in the refrigerator overnight.

The precipitated crystals are collected by filtration and are recrystallized from a mixture of methanol-ethanol to give β-diastereoisomer of 2,6-dimethyl-4-(m-nitrophenyl)-1,4-dihydropyridine-3,5-dicarboxylic acid-3-methylester-5-[1-phenyl-[2-[1-(4-ethoxycarbonyl)-piperazinyl]]ethyl]ester in the form of hydrochloride, as pale yellow crystals melting at 231.5° C. (decomposition). The mother liquor of crystallization is concentrated and acetone is added to the residue. The whole is allowed to stand in the refrigerator. The precipitated crystals are collected by filtration and recrystallized from a mixture solvent of methanol-ethanol to give α-diastereoisomer (hydrochloride ½ hydrate) as pale yellow crystals melting at 225.5° C. (decomposition).

EXAMPLE 3

To 55 ml of ethanol are added 9.87 g of 1-phenyl-2-piperidinoethyl acetoacetate, 3.9 g of methyl β-aminocrotonate and 6.0 g of 2,3-dichlorobenzaldehyde, and the mixture is refluxed under heating for 19 hours.

The reaction mixture is concentrated under reduced pressure. The residue is dissolved in chloroform and the chloroform layer is washed with a 5% aqueous solution of hydrochloric acid and a 5% aqueous solution of sodium carbonate, and then dried over magnesium sulfate. The chloroform is distilled off under reduced pressure and the residue is purified by column chromatography on silica gel (eluent:chloroform:ethyl acetate=95:5 (by volume)). The eluate is concentrated and the residue is dissolved in acetone whereupon an ethanol solution of hydrogen chloride is added to give the compound in the form of hydrochloride. The precipitated crystals are collected by filtration and recrystallized from methanol to give β-diastereoisomer of 2,6-dimethyl-4-(2,3-dichlorophenyl)-1,4-dihydropyridine-3,5-dicarboxylic acid-3-methylester-5-(1-phenyl-2-piperidinoethyl)ester in the form of hydrochloride as colorless crystals melting at 246° C. (decomposition).

The mother liquor of crystallization is concentrated. The residue is converted into the compound in the form of the base, followed by purification by column chromatography. The eluate is concentrated and the residue is dissolved in acetone whereupon an ethanol solution of hydrogen chloride is added to give the compound in the form of hydrochloride. Further, ether is added for crystallization. The precipitated crystals are collected by filtration and recrystallized from a mixture solvent of methanol-ethanol to give α-diastereoisomer (hydrochloride) as pale yellow crystals melting at 205°–206° C. (decomposition).

EXAMPLE 4

To 100 ml of ethanol are added 20.8 g of 1-phenyl-3-piperidinopropyl acetoacetate, 7.9 g of methyl β-aminocrotonate and 10.3 g of m-nitrobenzaldehyde, and the mixture is refluxed under heating for 16 hours. The reaction mixture is concentrated and the residue is dissolved in chloroform. The chloroform layer is washed with a 5% aqueous solution of hydrochloric acid and a 5% aqueous solution of sodium carbonate and dried over magnesium sulfate. Then, the chloroform is distilled off and the residue is purified by column chromatography on silica gel (eluent:chloroform:methanol=95:5 (by volume)). The firstly eluted solution is concentrated and the residue is dissolved in acetone. The precipitated crystals are collected by filtration and the crude crystals are recrystallized from a mixture solvent of methanol-ethanol to give α-diastereoisomer of 2,6-dimethyl-4-(m-nitrophenyl)-1,4-dihydropyridine-3,5-dicarboxylic acid-3-methylester-5-(1-phenyl-3-piperidinopropyl)ester in the form of hydrochloride as yellow crystals melting at 245° C.–246° C. (decomposition). The lastly eluted solution is treated in the same manner mentioned above to give β-diastereoisomer (hydrochloride ½ hydrate) as yellow crystals melting at 216° C. (decomposition).

EXAMPLE 5

In 350 ml of isopropanol are dissolved 30.9 g of 1-(2-thienyl)-2-piperidinoethyl acetoacetate, 15.4 g of m-nitrobenzaldehyde and 11.7 g of methyl β-aminocrotonate, and the mixture is refluxed under heating for 20 hours. The reaction mixture is concentrated under reduced pressure and the residue is purified by column chromatography on silica gel (eluent:chloroform:methanol=10:1.2 (by volume)). The firstly eluted solution is concentrated and recrystallized from ethanol to give 2,6-dimethyl-4-(m-nitrophenyl)-1,4-dihydropyridine-3,5-dicarboxylic acid-3-methylester-5-[1-(2-thienyl)-2-piperidinoethyl]ester as crystals melting at 179° C.–181° C. This is α-diastereoisomer and the hydrochloride therefore melts at 215° C.–218° C. (decomposition). The lastly eluted solution is concentrated and recrystallized from ethanol as crystals melting at 128° C.–134° C. The hydrochloride thereof melts at 188° C.–190° C. (decomposition).

EXAMPLE 6

To 130 ml of benzene are added 14.7 g of 1-phenyl-2-piperidinoethanol, 7.1 g of diketene and 1 ml of triethylamine. The mixture is refluxed under heating for three hours. The reaction mixture is concentrated under reduced pressure to give 22 g of 1-phenyl-2-piperidinoethyl acetoacetate. A mixture of 22 of 1-phenyl-2-piperidinoethyl acetoacetate, 10.6 g of m-nitrobenzaldehyde and 12.7 g of (2-furyl)methyl β-aminocrotonate in 130 ml of isopropanol is refluxed under heating for 12 hours. The reaction mixture is concentrated under reduced pressure. To the viscous jelly-like oily substance thus obtaned is added an ethanol solution of hydrogen chloride and then the mixture is concentrated. The viscous jelly-like residue is crystallized from a mixture solvent of acetone-ether. The precipitated crystals are collected by filtration, and recrystallized from a mixture solvent of acetone-methanol to give α-diastereoisomer of 2,6-dimethyl-4-(m-nitrophenyl)-1,4-dihydropyridine-3,5-dicarboxylic acid-3-(2-furyl)methylester-5-(1-phenyl-2-piperidinoethyl)ester in the form of hydrochloride as yellow crystals melting at 219°–221° C. (decomposition).

The mother liquor of crystallization is concentrated. The residue is converted into the compound in the form of the base, followed by purification by column chromatography on silica gel. The eluate is concentrated and the residue is crystallized from an ethanol solution of hydrogen chloride. The precipitated crystals are collected by filtration and are recrystallized from a mixture solvent of acetone-methanol to give β-diastereoisomer (hydrochloride) as yellow crystals melting at 211° C.–214° C. (decomposition).

EXAMPLE 7

To 300 ml of methanol are added 53 g of phenacyl bromide, 25 g of 3-methylpiperidine and 37 g of potassium carbonate, and the mixture is subjected to reaction at room temperature for two hours. The insoluble substances in the reaction mixture are filtered off and to the filtrate is added 7.1 g of sodium borohydride at room temperature and the mixture is stirred for two hours. The reaction mixture is concentrated under reduced pressure. The oily substance thus obtained is dissolved in ethyl acetate.

The solution is washed with water and then extracted with 1N-hydrochloric acid. The water layer is washed with ethyl acetate and is adjusted to pH 10 with potassium carbonate. The separate oily substance is extracted with ethyl acetate. The extract layer is washed with water and then dried over magnesium sulfate. The ethyl acetate layer is concentrated under reduced pressure and recrystallized three times from isopropyl ether to give 2-(3-methylpiperidino)-1-phenylethanol melting at 70° C. Meanwhile, the mother liquor of the above recrystallization is concentrated under reduced pressure and the residue is dissolved in isopropanol, whereupon an ethanol solution of hydrogen chloride is added to give the compound in the form of hydrochloride. The precipitated crystals are collected by filtration and recrystallized twice from isopropanol to give the other diastereoisomer in the form of hydrochloride melting at 195°–196° C.

To 100 ml of benzene are added 9.5 g of 2-(3-methyl piperidino)-1-phenylethanol having a melting point of 70° C., 5 g of diketene and 0.1 ml of triethylamine, and the mixture is refluxed under heating for two hours. The reaction mixture is concentrated under reduced pressure to give 14 g of 2-(3-methylpiperidino)-1-phenylethyl acetoacetate as oily substance. To 150 ml of isopropanol are added 14 g of 2-(3-methylpiperidino)-1-phenylethyl acetoacetate, 6.5 g of m-nitrobenzaldehyde and 5 g of methyl β-aminocrotonate, and the mixture is refluxed under heating for 15 hours. The reaction mixture is concentrated under reduced pressure and the oily residue is dissolved in ethyl acetate. The ethyl acetate layer is washed with 1N-hydrochlroic acid, potassium carbonate and water, then dried over anhydrous magnesium sulfate and concentrated under reduced pressure. The oily residue (25 g) is purified by column chromatography. The eluate is concentrated and the residue is dissolved in acetone, whereupon an ethanol solution of hydrogen chloride is added to crystallize. The precipitated crystals are collected by filtration and recrystallized from ethanol to give 2,6-dimethyl-4-(m-nitrophenyl)-1,4-dihydropyridine-3,5-dicarboxylic acid-3-methylester-5-[2-(3-methylpiperidino)-1-phenyl]ester in the form of hydrochloride as crystals melting at 225° C.–226° C. (decomposition).

Meanwhile, the other eluted solution is treated in the same manner as mentioned above to give the other diastereoisomer in the form of hydrochloride as crystals melting at 222° C.–223° C. (decomposition).

Furthermore, by the use of 2-(3-methylpiperidino)-1-phenylethanol hydrochloride having a melting point of 195°–196° C. as a starting compound, two kinds of diastereoisomers of the object compound in the form of hydrochloride can be obtained as crystals melting at 195°–196° C. (decomposition) and as crystals melting at 242° C. (decomposition) by subjecting the same reaction and post-treatment as mentioned above.

The following compounds can be also produced in the same manner as the examples set forth above.

(1) 2,6-dimethyl-4-(m-nitrophenyl)-1,4-dihydropyridine-3,5-dicarboxylic acid-3-methylester-5-[1-phenyl-2-(1-pyrrolidinyl)ethyl]ester, α-diastereoisomer: m.p 158°–159° C., hydrochloride thereof: m.p. 237° C. (decomposition); β-diastereoisomer: m.p. 162°–163° C., hydrochloride thereof: m.p. 228°–230° C. (decomposition)

(2) 2,6-dimethyl-4-(m-nitrophenyl)-1,4-dihydropyridine-3,5-dicarboxylic acid-3-methylester-5-[2-(hexahydroazepin-1-yl)-1-phenylethyl]ester, α-diastereoisomer: m.p. 148°–151° C., hydrochloride thereof: m.p. 228°–230° C. (decomposition); β-diastereoisomer: m.p. 153°–155° C., hydrochloride thereof: m.p. 188°–191° C. (decomposition)

(3) 2,6-dimethyl-4-(m-nitrophenyl)-1,4-dihydropyridine-3,5-dicarboxylic acid-3-methylester-5-(2-morpholino-1-phenylethyl)ester, α-diastereoisomer: m.p. 166°–170° C., hydrochloride thereof: m.p. 156°–160° C. (decomposition); β-diastereoisomer: m.p. 130°–133° C., hydrochloride thereof: m.p. 216°–219° C. (decomposition)

(4) 2,6-dimethyl-4-(m-nitrophenyl)-1,4-dihydropyridine-3,5-dicarboxylic acid-3-methylester-5-(1-phenyl-2-thiomorpholinoethyl)ester, α-diastereoisomer: m.p. 166°–168° C., hydrochloride thereof: m.p. 223°–224° C. (decomposition); β-diastereoisomer: m.p. 148°–150° C., hydrochloride thereof: m.p. 221°–222° C., (decomposition)

(5) 2,6-dimethyl-4-(m-nitrophenyl)-1,4-dihydropyridine-3,5-dicarboxylic acid-3-methylester-5-[2-[1-(4-methylpiperazinyl)]-1-phenylethyl]ester difumarate, β-diastereoisomer: m.p. 175°–180° C. (decomposition)

(6) 2,6-dimethyl-4-(o-chlorophenyl)-1,4-dihydropyridine-3,5-dicarboxylic acid-3-methylester-5-(1-phenyl-2-piperidinoethyl)ester hydrochloride: m.p. 232°–234° C. (decomposition)

(7) 2,6-dimethyl-4-(m-nitrophenyl)-1,4-dihydropyridine-3,5-dicarboxylic acid-3-isopropylester-5-(1-phenyl-2-piperidinoethyl)ester, α-diastereoisomer (hydrochloride ½ hydrate): m.p. 217°–219° C. (decomposition); β-diastereoisomer (hydrochloride): m.p. 165°–167° C. (decomposition)

(8) 2,6-dimethyl-4-(m-nitrophenyl)-1,4-dihydropyridine-3,5-dicarboxylic acid-3-benzylester-5-(1-phenyl-2-piperidinoethyl)ester, α-diastereoisomer (hydrochloride): m.p. 213°–214° C. (decomposition); β-diastereoisomer (hydrochlroide): m.p. 212°–213° C. (decomposition)

(9) 2,6-dimethyl-4-(m-nitrophenyl)-1,4-dihydropyridine-3,5-dicarboxylic acid-3-methylester-5-(1-phenyl-4-piperidinobutyl)ester

(10) 2,6-dimethyl-4-(m-nitrophenyl)-1,4-dihydropyridine-3,5-dicarboxylic acid-3-methylester-5-[1-(o-chlorophenyl)-2-piperidinoethyl]ester, α-diastereoisomer (hydrochloride): m.p. 218°–219° C. (decomposition); β-diastereoisomer (hydrochloride): m.p. 231°–232° C. (decomposition)

(11) 2,6-dimethyl-4-(m-nitrophenyl)-1,4-dihydropyridine-3,5-dicarboxylic acid-3-methylester-5-[1-(p-chlorophenyl)-2-piperidinoethyl]ester, α-diastereoisomer: m.p. 174°–176° C., hydrochloride thereof: m.p. 205°–207° C.; β-diastereoisomer: m.p. 128°–130° C., hydrochloride thereof: m.p. 205°–207° C. (decomposition)

(12) 2,6-dimethyl-4-(m-nitrophenyl)-1,4-dihydropyridine-3,5-dicarboxylic acid-3-methylester-5-[1-(o-methylphenyl)-2-piperidinoethyl]ester, α-diastereoisomer (hydrochloride): m.p. 224°–225° C. (decomposition); β-diastereoisomer (hydrochloride): m.p. 235°–236° C. (decomposition)

(13) 2,6-dimethyl-4-(m-nitrophenyl)-1,4-dihydropyridine-3,5-dicarboxylic acid-3-methylester-5-[1-(p-methylphenyl)-2-piperidinoethyl]ester, α-diastereoisomer: m.p. 143°–145.5° C., hydrochloride thereof: m.p. 168°–170° C. (decomposition); β-diastereoisomer: m.p. 122°–124° C., hydrochloride thereof: m.p. 209°–209.5° C. (decomposition)

(14) 2,6-dimethyl-4-(m-nitrophenyl)-1,4-dihydropyridine-3,5-dicarboxylic acid-3-methylester-5-[1-(p-fluorophenyl)-2-piperidinoethyl]ester, α-diastereoisomer (hydrochloride ½ hydrate): m.p. 186°–187° C. (decomposition); β-diastereoisomer (hydrochloride): m.p. 195°–196° C. (decomposition)

(15) 2,6-dimethyl-4-(m-nitrophenyl)-1,4-dihydropyridine-3,5-dicarboxylic-3-methylester-5-[1-(p-methoxyphenyl)-2-piperidinoethyl]ester, α-diastereoisomer: m.p. 162°–164° C.; β-diastereoisomer (hydrochloride): m.p. 204°–205° C. (decomposition)

(16) 2,6-dimethyl-4-(m-nitrophenyl)-1,4-dihydropyridine-3,5-dicarboxylic acid-3-methylester-5-[2-(2-methylpiperidino)-1-phenylethyl]ester, α-diastereoisomer (hydrochloride): m.p. 226°–226.5° C. (decomposition); β-diastereoisomer (hydrochloride): m.p. 222° C. (decomposition)

(17) 2,6-dimethyl-4-(m-nitrophenyl)-1,4-dihydropyridine-3,5-dicarboxylic acid-3-methylester-5-[2-(4-methylpiperidino)-1-phenylethyl]ester, α-diastereoisomer (hydrochloride): m.p. 216°–219° C. (decomposition); β-diastereoisomer (hydrochloride): m.p. 227°–228° C. (decomposition)

(18) 2,6-dimethyl-4-(m-nitrophenyl)-1,4-dihydropyridine-3,5-dicarboxylic acid-3-methylester-5-[2-(4-hydroxypiperidino)-1-phenylethyl]ester, α-diastereoisomer (monofumarate): m.p. 144°–147° C. (decomposition); β-diastereoisomer (hydrochloride ½ hydrate): m.p. 222°–223° C. (decomposition)

(19) 2,6-dimethyl-4-(m-nitrophenyl)-1,4-dihydropyridine-3,5-dicarboxylic acid-3-methylester-5-[2-(4-acetyloxypiperidino)-1-phenylethyl]ester, α-diastereoisomer (hydrochloride): m.p. 200°–202° C. (decomposition; β-diastereoisomer (hydrochloride): m.p. 223°–226° C. (decomposition)

(20) 2,6-dimethyl-4-(m-nitrophenyl)-1,4-dihydropyridine-3,5-dicarboxylic acid-3-methylester-5-[2-(4-acetylaminopiperidino)-1-phenylethyl]ester, β-diastereoisomer (monofumarate): m.p. 218°–220° C. (decomposition)

(21) 2,6-dimethyl-4-(m-nitrophenyl)-1,4-dihydropyridine-3,5-dicarboxylic acid-3-methylester-5-[2-(4-methoxypiperidino)-1-phenylethyl]ester, α-diastereoisomer (hydrochloride): m.p. 235°–236° C. (decomposition); β-diastereoisomer hydrochloride): m.p. 248°–249° C. (decomposition)

(22) 2,6-dimethyl-4-(m-nitrophenyl)-1,4-dihydropyridine-3,5-dicarboxylic acid-3-methylester-5-[2-(4,4-ethylenedioxypiperidino)-1-phenylethyl]ester, α-diastereoisomer (hydrochloride monohydrate): m.p. 205°–207° C. (decomposition); β-diastereoisomer (hydrochloride): m.p. 233°–235° C. (decomposition)

(23) 2,6-dimethyl-4-(m-nitrophenyl)-1,4-dihydropyridine-3,5-dicarboxylic acid-3-methylester-5-[2-[1-(1,2,3,6-tetrahydropyridyl)]-1-phenylethyl]ester, α-diastereoisomer: m.p. 168°–171° C., hydrochloride thereof: m.p. 235°–237° C. (decomposition); β-diastereoisomer: m.p. 122°–126° C., hydrochloride thereof: m.p. 210°–213° C. (decomposition)

(24) 2,6-dimethyl-4-(m-nitrophenyl)-1,4-dihydropyridine-3,5-dicarboxylic acid-3-methylester-5-[1-(2-furyl)-2-piperidinoethyl]ester, α-diastereoisomer: m.p. 182°–185° C., hydrochloride thereof: m.p. 190°–193° C. (decomposition); β-diastereoisomer: m.p. 104°–107° C., hydrochloride thereof: m.p. 138°–142° C. (decomposition)

(25) 2,6-dimethyl-4-(o-nitrophenyl)-1,4-dihydropyridine-3,5-dicarboxylic acid-3-methylester-5-(1-phenyl-2-piperidinoethyl)ester, α-diastereoisomer (hydrochloride): m.p. 233°–234° C. (decomposition)

(26) 2,6-dimethyl-4-(m-nitrophenyl)-1,4-dihydropyridine-3,5-dicarboxylic acid-3-methylester-5-[1-(3-pyridyl)-2-piperidinoethyl]ester dihydrochloride ½ hydrate: m.p. 200.5°–202° C. (decomposition)

(27) 2,6-dimethyl-4-(m-nitrophenyl)-1,4-dihydropyridine-3,5-dicarboxylic acid-3-methylester-5-[2-piperidino-1-(2-pyrrolyl)ethyl]ester

(28) 2,6-dimethyl-4-(m-nitrophenyl)-1,4-dihydropyridine-3,5-dicarboxylic acid-3-methylester-5-[1-methyl-2-pyrrolyl)-2-piperidinoethyl]ester

(29) 2,6-dimethyl-4-(m-nitrophenyl)-1,4-dihydropyridine-3,5-dicarboxylic acid-3-methylester-5-[1-(1-methyl-2-imidazolyl)-2-piperidinoethyl]ester

(30) 2,6-dimethyl-4-(m-nitrophenyl)-1,4-dihydropyridine-3,5-dicarboxylic acid-3-methylester-5-[2-piperidino-1-(2-thiazolyl)ethyl]ester

(31) 2,6-dimethyl-4-(m-nitrophenyl)-1,4-dihydropyridine-3,5-dicarboxylic acid-3-methylester-5-[1-(2-oxazolyl)-2-piperidinoethyl]ester

(32) 2,6-dimethyl-4-(2-chloro-5-nitrophenyl)-1,4-dihydropyridine-3,5-dicarboxylic acid-3-methylester-5-(1-phenyl-2-piperidinoethyl ester, α-diastereoisomer (hydrochloride): m.p. 233°-234° C. (decomposition); β-diastereoisomer (hydrochloride): m.p. 175°-178° C. (decomposition)

(33) 2,6-dimethyl-4-(2-thienyl)-1,4-dihydropyridine-3,5-dicarboxylic acid-3-methylester-5-(1-phenyl-2-piperidinoethyl)ester, α-diastereoisomer (hydrochloride): m.p. 232° C. (decomposition); β-diastereoisomer (hydrochloride): m.p. 233°-234° C. (decomposition)

(34) 2,6-dimethyl-4-(2-furyl)-1,4-dihydropyridine-3,5-dicarboxylic acid-3-methylester-5-(1-phenyl-2-piperidinoethyl)ester, α-diastereoisomer (hydrochloride): m.p. 196°-198° C. (decomposition); β-diastereoisomer (hydrochloride): m.p. 216°-217° C. (decomposition)

(35) 2,6-dimethyl-4-(o-trifluoromethylphenyl)-1,4-dihydropyridine-3,5-dicarboxylic acid-3-methylester-5-(1-phenyl-2-piperidinoethyl)ester

(36) 2,6-dimethyl-4-(o-cyanophenyl)-1,4-dihydropyridine-3,5-dicarboxylic acid-3-methylester-5-(1-phenyl-2-piperidinoethyl)ester

(37) 2,6-dimethyl-4-(o-methylthiophenyl)-1,4-dihydropyridine-3,5-dicarboxylic acid-3-methylester-5-(1-phenyl-2-piperidinoethyl)ester

(38) 2,6-dimethyl-4-(2-pyridyl)-1,4-dihydropyridine-3,5-dicarboxylic acid-3-methylester-5-(1-phenyl-2-piperidinoethyl)ester, α-diastereoisomer (dihydrochloride): m.p. 260°-265° C. (decomposition); β-diastereoisomer (hydrochloride): m.p. 170°-175° C. (decomposition)

(39) 2,6-dimethyl-4-(2-pyrrolyl)-1,4-dihydropyridine-3,5-dicarboxylic acid-3-methylester-5-(1-phenyl-2-piperidinoethyl)ester

(40) 2,6-dimethyl-4-(1-methyl-2-pyrrolyl)-1,4-dihydropyridine-3,5-dicarboxylic acid-3-methylester-5-(1-phenyl-2-piperidinoethyl)ester

(41) 2,6-dimethyl-4-(2-pyrrolyl)-1,4-dihydropyridine-3,5-dicarboxylic acid-3-methylester-5-(1-phenyl-2-piperidinoethyl)ester, β-diastereoisomer (fumarate ½ hydrate): m.p. 141°-143° C. (decomposition)

(42) 2,6-dimethyl-4-(3-thienyl)-1,4-dihydropyridine-3,5-dicarboxylic acid-3-methylester-5-(1-phenyl-2-piperidinoethyl)ester, α-diastereoisomer (hydrochloride): m.p. 238°-239° C. (decomposition); β-diastereoisomer (hydrochloride ½ hydrate): m.p. 234°-236° C.

(43) 2,6-dimethyl-4-(5-methyl-2-furyl)-1,4-dihydropyridine-3,5-dicarboxylic acid-3-methylester-5-(1-phenyl-2-piperidinoethyl)ester, α-diastereoisomer (hydrochloride): m.p. 214°-216° C. (decomposition); β-diastereoisomer (hydrochloride): m.p. 220° C. (decomposition)

(44) 2,6-dimethyl-4-(2-furyl)-1,4-dihydropyridine-3,5-dicarboxylic acid-3-methylester-5-[2-piperidino-1-(2-thienyl)ethyl]ester, α-diastereoisomer (hydrochloride): m.p. 205°-207° C. (decomposition); β-diastereoisomer (hydrochloride): m.p. 215°-217° C. (decomposition)

(45) 2,6-dimethyl-4-(3-pyridyl)-1,4-dihydropyridine-3,5-dicarboxylic acid-3-methylester-5-(1-phenyl-2-piperidinoethyl)ester, α-diastereoisomer (hydrochloride): m.p. 225°-227° C. (decomposition); β-diastereoisomer (maleate): m.p. 210°-215° C. (decomposition)

(46) 2,6-dimethyl-4-(2-imidazolyl)-1,4-dihydropyridine-3,5-dicarboxylic acid-3-methylester-5-(1-phenyl-2-piperidinoethyl)ester, α-diastereoisomer (dihydrochloride 3/2 hydrate): m.p. 211.5°-212° C. (decomposition); β-diastereoisomer (dihydrochloride dihydrate): m.p. 227°-228° C. (decomposition)

(47) 2,6-dimethyl-4-(2-thiazolyl)-1,4-dihydropyridine-3,5-dicarboxylic acid-3-methylester-5-(1-phenyl-2-piperidinoethyl)ester, α-diastereoisomer (dihydrochloride ⅓ hydrate): m.p. 192° C. (decomposition); β-diastereoisomer (hydrochloride): m.p. 214°-215° C.

(48) 2,6-dimethyl-4-(pyridine-N-oxide-3-yl)-1,4-dihydropyridine-3,5-dicarboxylic acid-3-methylester-5-(1-phenyl-2-piperidinoethyl)ester, α-diastereoisomer (difumarate): m.p. 151°-153° C. (decomposition); β-diastereoisomer (dihydrochloride): m.p. 180°-185° C. (decomposition)

EXAMPLES OF PHARMACEUTICAL PREPARATIONS

Tablets (5 mg) are prepared from the following compositions:

| | |
|---|---|
| α-diastereoisomer of Example 1 | 5.0 mg |
| Lactose | 62.3 mg |
| Cornstarch | 25.0 mg |
| Microcrystalline Cellulose | 6.0 mg |
| Methyl Cellulose | 1.0 mg |
| Magnesium Stearate | 0.7 mg |
| | 100.0 mg |

Powders (1% by weight) are prepared from the following compositions:

| | |
|---|---|
| α-diastereoisomer of Example 1 | 1.0% by weight |
| Lactose | 88.0% |
| Microcrystalline Cellulose | 10.0% |
| Methyl Cellulose | 1.0% |
| | 100.0% |

While the invention has been described in detail and with reference to specific embodiments thereof, it is apparent that various alterations and modifications can be made without departing from the spirit and scope thereof.

What is claimed is:

1. A 1,4-dihydropyridine-3,5-dicarboxylic acid ester derivative of the general formula:

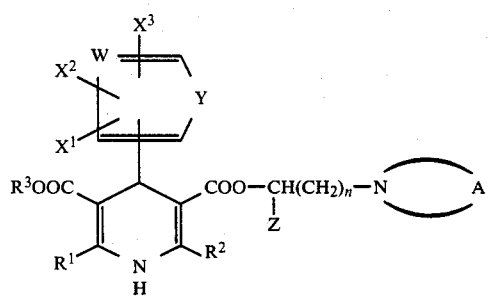

or a pharmaceutically acceptable acid addition salt thereof, wherein W is —CH=; Y is —CH=CH—, —O—, —S—, —CH=N or —N(R)— (R is hydrogen or lower alkyl); $X^1$, $X^2$ and $X^3$ are the same or different, and are each hydrogen, halogen, nitro, trifluoromethyl, cyano or lower alkylthio; Z is aryl or 5- or 6-membered aromatic heterocyclic ring (which may have a substituent or two or three substituents which are the same or different, and the substituent may be halogen, lower alkyl, lower alkoxy, lower alkanoylamino, cyano, nitro, lower alkylthio, trifluoromethyl, sulfamoyl, di-lower alkyl-sulfamoyl, amino or di-lower alkylamino);

is 5- to 7-membered heterocyclic ring which may have nitrogen atom, oxygen atom, or sulfur atom on the ring and may be substituted by lower alkyl, lower alkoxycarbonyl, lower alkanoylamino, ethylenedioxy or —(CH$_2$)$_m$—OR$^4$ (R$^4$ is hydrogen, lower alkyl or lower alkanoyl and m is 0, 1 or 2); R$^1$ and R$^2$ are the same or different and are each lower alkyl; R$^3$ is lower alkyl, aralkyl or heteroalkyl; and n is an integer 1 to 5.

2. The compound of claim 1: 2,6-dimethyl-4-(m-nitrophenyl)-1,4-dihydropyridine-3,5-dicarboxylic acid-3-methylester-5-(1-phenyl-2-piperidinoethyl)ester.

3. The compound of claim 1: 2,6-dimethyl-4-(m-nitrophenyl)-1,4-dihydropyridine-3,5-dicarboxylic acid-3-methylester-5-[1-(2-thienyl)-2-piperidinoethyl]ester.

4. The compound of claim 1: 2,6-dimethyl-4-(m-nitropheny)-1,4-dihydropyridine-3,5-dicarboxylic acid-3-methylester-5-[1-(2-furyl)-2-piperidinoethyl]ester.

5. The compound of claim 1: 2,6-dimethyl-4-(2-thienyl)-1,4-dihydropyridine-3,5-dicarboxylic acid-3-methylester-5-(1-phenyl-2-piperidinoethyl)ester.

6. The compound of claim 1: 2,6-dimethyl-4-(2-furyl)-1,4-dihydropyridine-3,5-dicarboxylic acid-3-methylester-5-(1-phenyl-2-piperidinoethyl)ester.

7. A pharmaceutical composition comprising the compound of claim 1 in combination with a pharmaceutically acceptable inert carrier, said compound being present in a therapeutically effective amount.

* * * * *